United States Patent [19]

Cole et al.

[11] Patent Number: 4,870,287

[45] Date of Patent: Sep. 26, 1989

[54] MULTI-STATION PROTON BEAM THERAPY SYSTEM

[75] Inventors: Francis T. Cole, Wheaton; Philip V. Livdahl; Frederick E. Mills, III, both of Elburn; Lee C. Teng, Hinsdale, all of Ill.

[73] Assignee: Loma Linda University Medical Center, Loma Linda, Calif.

[21] Appl. No.: 163,611

[22] Filed: Mar. 3, 1988

[51] Int. Cl.⁴ .............................................. G21G 1/10
[52] U.S. Cl. ................................ 250/492.3; 250/398; 328/235
[58] Field of Search .......... 250/492.3, 496.1, 396 ML, 250/306, 307, 251; 328/233, 235, 234

[56] References Cited

U.S. PATENT DOCUMENTS

| | | | |
|---|---|---|---|
| 3,986,026 | 10/1976 | Martin | 250/306 |
| 4,069,457 | 1/1978 | Martin et al. | 328/235 |
| 4,112,306 | 9/1978 | Nunan | 328/234 |
| 4,287,425 | 9/1981 | Elliot, Jr. | 250/398 |
| 4,442,352 | 4/1984 | Brahme | 250/251 |

OTHER PUBLICATIONS

J. Archambeau et al., "Design of a Proton Therapy Synchrotron", Fermi National Accelerator Laboratory, Jun. 1986.

Primary Examiner—Janice A. Howell
Assistant Examiner—Michael Aronoff
Attorney, Agent, or Firm—Robert R. Meads

[57] ABSTRACT

A proton beam therapy system for selectively generating and transporting proton beams from a single proton source and accelerator to selected ones of a plurality of patient treatment stations each having a rotatable gantry for delivering the proton beam at different angles to patients supported in fixed orientations at the stations.

2 Claims, 7 Drawing Sheets 4,870,287

MULTI-STATION PROTON BEAM THERAPY SYSTEM

BACKGROUND

The present invention relates to a multi-station proton beam therapy system useful in the treatment of cancer.

In 1945, R. R. Wilson proposed the use of proton beams in the treatment of cancer. {Radiology 47, 487 (1946)}. The advantage of protons in such treatment resides in the following physical characteristics (1) the radiation dose delivered by a proton penetrating tissue rises as the proton slows down, reaching a maximum near its stopping point ("Bragg peak"), and is zero beyond the stopping point, (2) protons in a monoenergetic beam have nearly the same range and therefore deliver a maximum dose at the same depth, and (3) protons being relatively heavy do not deviate much from a straight line as they come to rest.

Today, proton beam therapy is in use at the Harvard Cyclotron Laboratory in association with Massachusetts General Hospital in Boston, Mass., in Japan at KKK and Chiba, and in the USSR at ITEP-Moscow, at JINR-Dubna, and at Gatchina near Leningrad. At each of these facilities, however, proton therapy uses an accelerator that was designed and built for physics research, and has now been adapted to do part-time clinical ion proton beam irradiation.

To realize the full potential of the proton beam in the treatment of cancer and other diseases responsive to radiation treatment, it is necessary for the physician to known the exact location of the site to be treated and the characteristics of the tissue overlying the treatment site. It is only with advent of new imaging techniques such as computed tomography (CT scanning) and magnetic resonance imaging (MRI) that such information is now available with the required accuracy. A full-time proton therapy facility for the treatment of cancer patients now appears to be feasible.

SUMMARY OR INVENTION

The present invention provides a dedicated proton beam therapy system including a plurality of separate treatment stations served from a single proton source and proton beam accelerator. At each treatment station is a patient support and gantry for delivering a beam of protons from many different angles to a patient supported in a fixed orientation. The proton beam is directed from the accelerator to the patient in the treatment station by a beam transport system. The beam transport system includes the gantry in each treatment station and a proton beam switchyard. An operator regulated control system controls the switchyard to select which treatment station is to receive the proton beam at any given time. To this end, the switchyard includes at least one proton beam switching magnet which is responsive to the control system for selectively switching the proton beam from a straight ahead beam line into the gantry of the selected treatment station. Optics carried by the gantry receive the proton beam on an axis of rotation of the gantry, transport the beam away from the axis and return the beam on a path perpendicular to and intersecting the axis at a target isocenter within the patient to be treated. By rotating the gantry under control of the control system the proton beam is delivered to the target isocenter from several different directions during treatment of the patient.

DETAILED DESCRIPTION OF INVENTION

The proton beam therapy system illustrated generally in FIGS. 1-7 is described and illustrated in detail in a publication entitled "Loma Linda University Medical Center Proton Therapy Facility Engineering Design Report February 1987." The publication was prepared for Loma Linda University Medical Center by Fermi National Accelerator Laboratory and was delivered to Loma Linda University Medical center on Mar. 4, 1987, and thereafter to others. In order to complete the detailed description of the invention in accord with 35 USC 112 and 37 CFR 1.71, the foregoing publication is hereby incorporated in its entirety into this specification and should be consulted for a more complete understanding of the invention.

Figure 1:
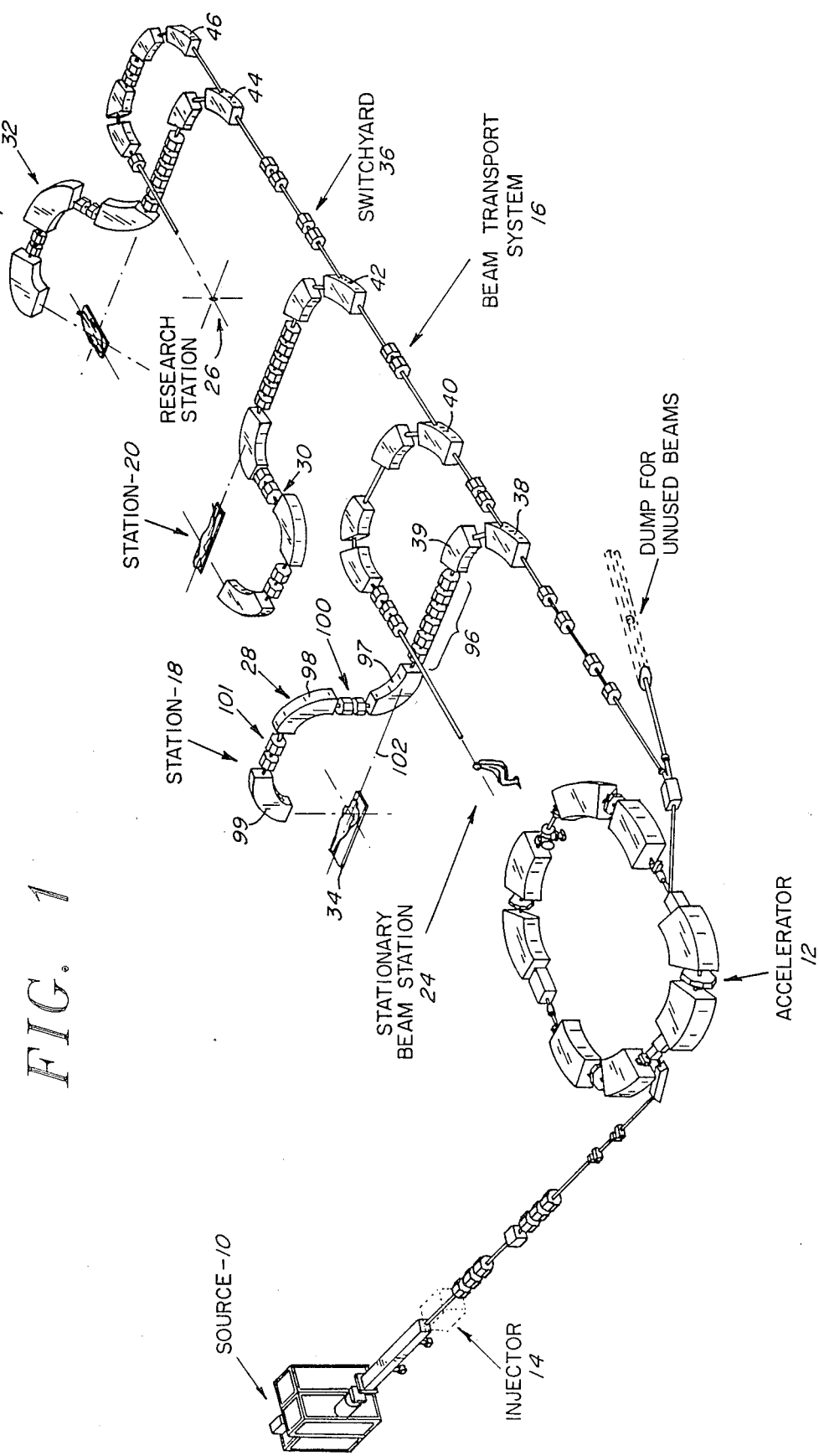
FIG. 1 is an isometric view of the structure of the proton beam therapy system of the present invention.
Figure 2:
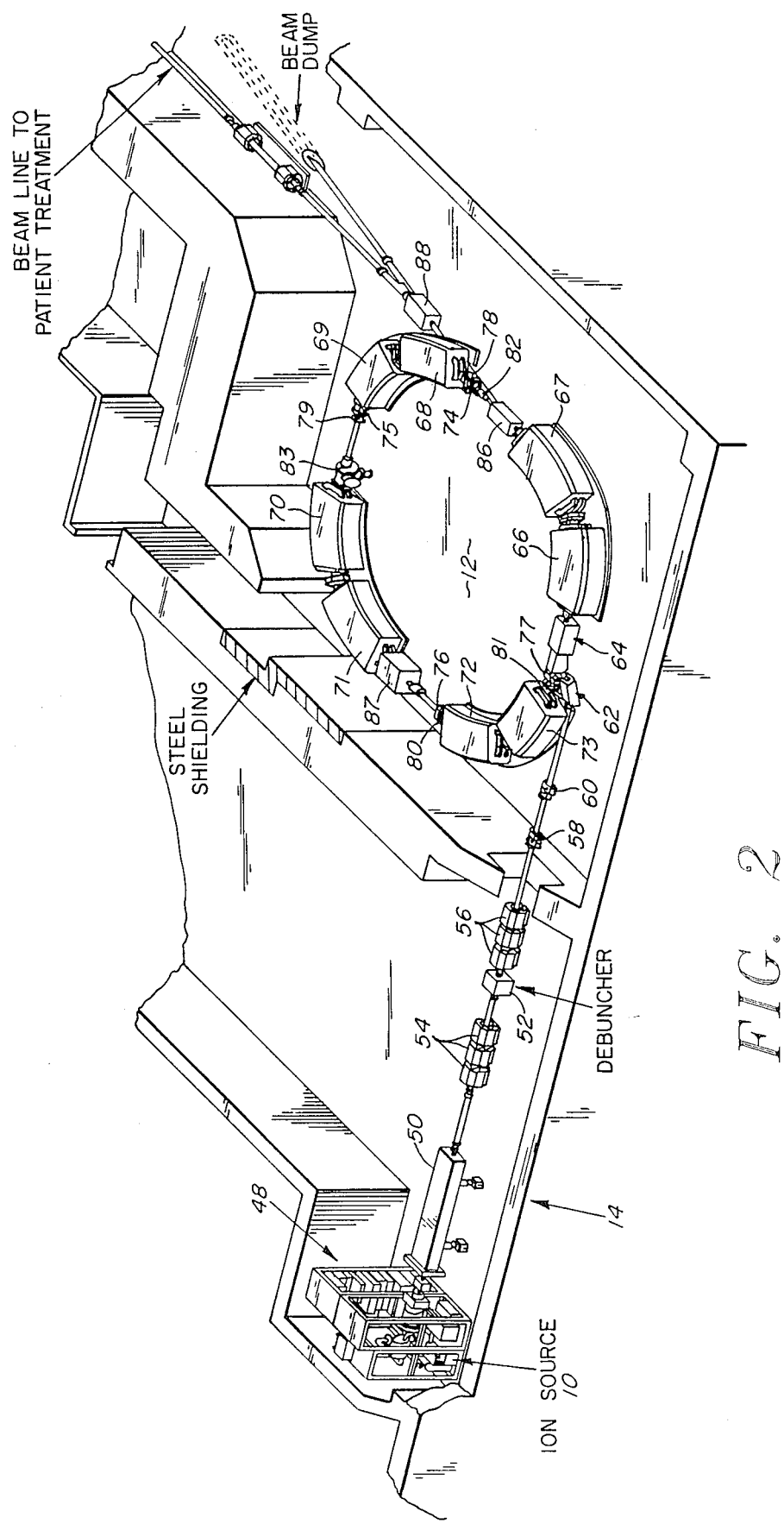
FIG. 2 a slightly enlarged view of the proton source, injector and accelerator shown in FIG. 1.
Figure 3:
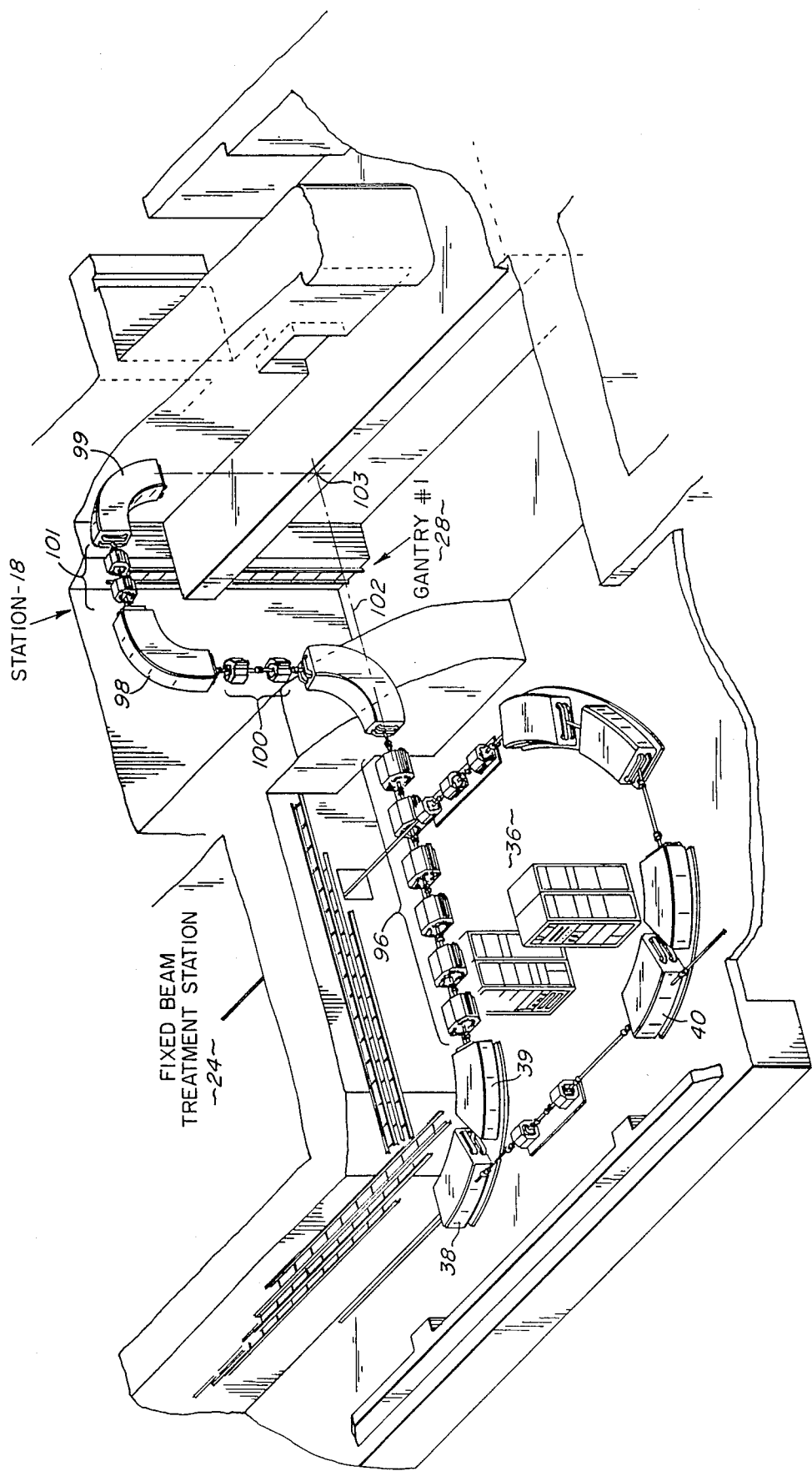
FIG. 3 is a slightly enlarged view of the switchyard and gantry #1 shown in FIG. 1.
Figure 4:
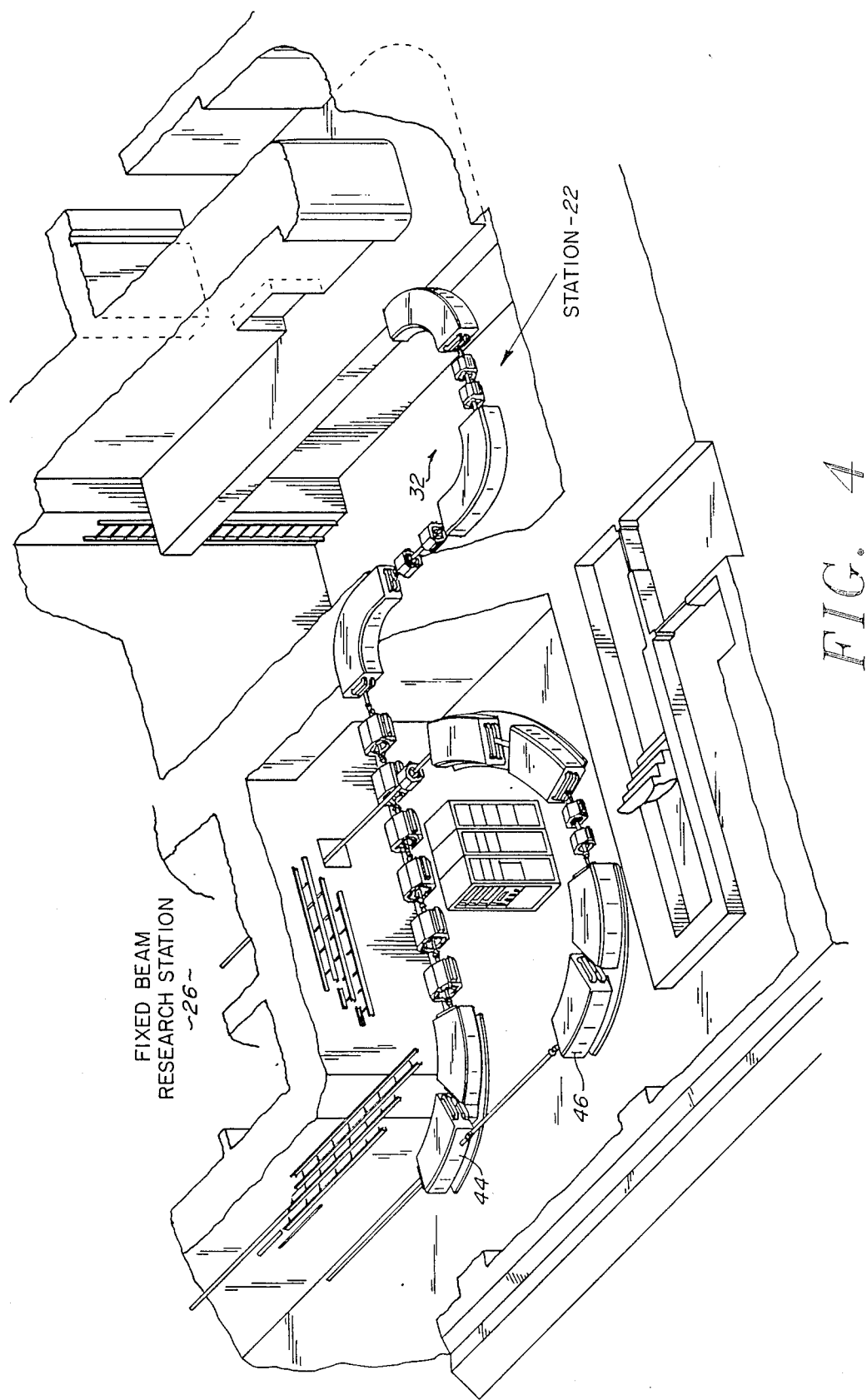
FIG. 4 is a slightly enlarged view of gantry #3 shown in FIG. 1.
Figure 5:
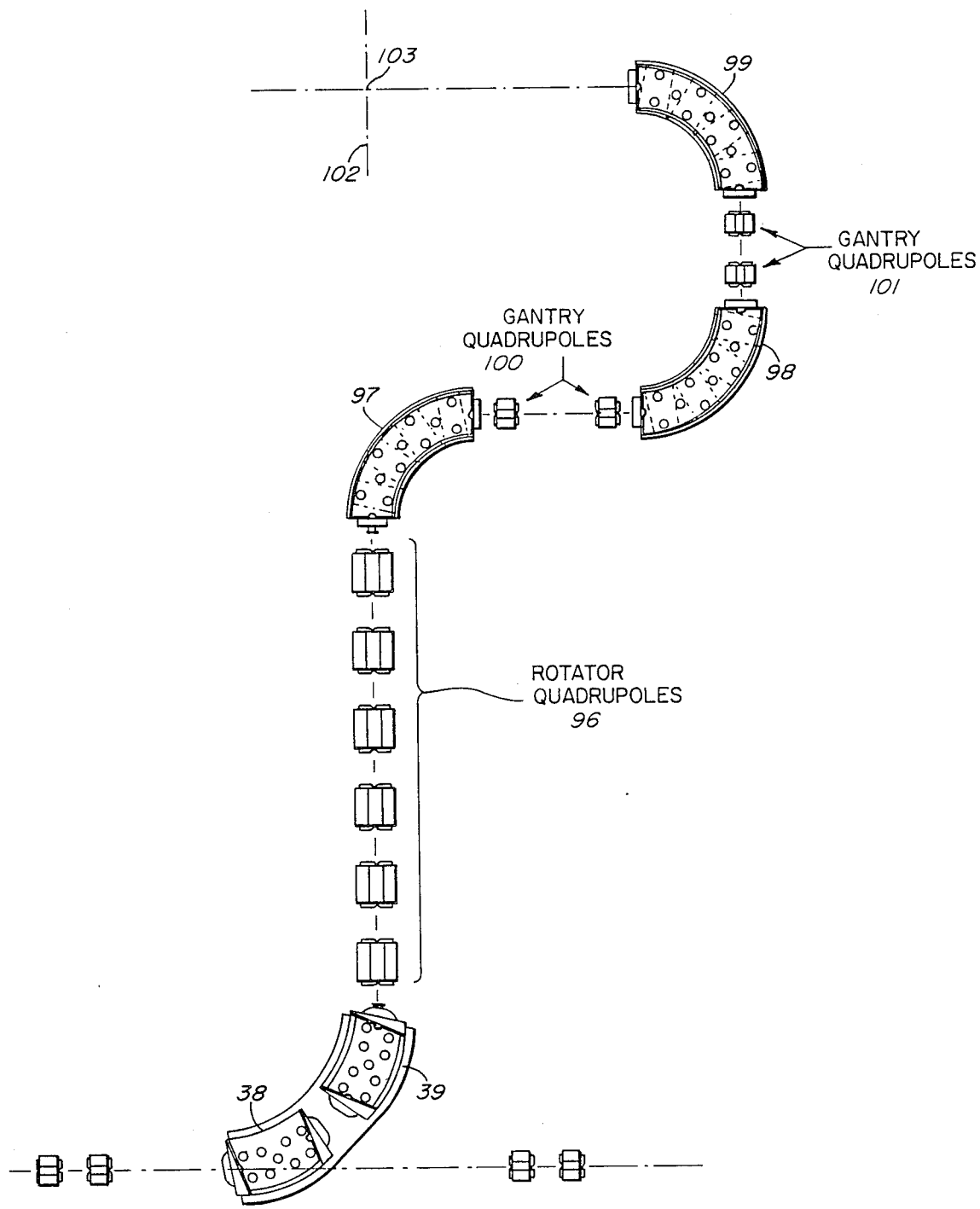
FIG. 5 is an exploded view of a gantry included in the system of FIG. 1.

Generally speaking, as illustrated in FIG. 1, the proton beam therapy system of the present invention comprises a proton source 10 connected to an accelerator 12 by an injector 14. The accelerator 12 accelerates the protons in a beam and via a beam transport system 16 delivers the proton beam to patients supported in fixed orientations in selected ones of a plurality of treatment stations 18, 20, 22, and 24 or to a research beam station 26. In the foregoing operation, the proton beam therapy system is under operator control via the computer control system illustrated in FIG. 6. At the treatment stations 18, 20 and 22, the beam transport system 16 includes gantries 28, 30 and 32 respectively, each rotatable about a different axis of rotation and carrying optics as illustrated in FIG. 5 for receiving a proton beam on its axis of rotation, transporting the proton beam away from the axis of rotation and returning the proton beam on a path perpendicular to and intersecting the axis of rotation at a target isocenter within a patient supported in a fixed orientation by a patient support, such as table 34. Thus arranged, upon a rotation of the gantry, the proton beam is delivered to the target isocenter from several different angles during patient treatment.

The illustrated beam handling system 16 also includes a switchyard 36 comprising four switching magnets 38, 40, 42 and 44. Each switching magnet is characterized by two states and is electronically switchable between its two states in response to operator control of the system illustrated in FIG. 7. In the first state, switching magnet 38 for example will receive the proton beam from the accelerator 12 and bend and deliver the proton beam to the optics carried by the gantry 28 along the axis of rotation of gantry 28. In the second state, switching magnet 38 will pass the proton beam to the switching magnet 40 which in its first state will bend and deliver the proton beam to components in the beam handling system for directing the proton beam to a stationary beam treatment station. In the second state for the switching magnet 40, it will pass the proton beam to the switching magnet 42. Like switching magnet 38, when switching magnet 42 is in its first state it will bend and direct the proton beam to the optics carried by the gantry 30 along the axis of rotation of gantry 30. In its second state, switching magnet 42 will pass the proton beam to the switching magnet 44 which in its first state will bend and deliver the beam to the optics carried by the gantry 32 along the axis of rotation of gantry 32. In its second state the switching magnet will pass the beam to a magnet 46 for bending and direction to a beam research station.

More specifically, in the construction of the proton beam therapy system of the present invention, conventional components are utilized, combined, adjusted and fine-tuned according to well known ion beam transport, acceleration and focusing techniques to achieve the accelerator and injection system parameters listed in Appendix I and Appendix II and the performance specifications and parameters listed in Tables I–VII set forth at the end of this specification. As there listed, the source 10 comprises a duoplasmatron ion source providing a 40 keV proton beam. The beam is focused by solenoidal lenses at 48 to match the beam into a radio-frequency quadrupole linear accelerator (RFQ) 50. The RFQ 50 accelerates protons to 1.7 MeV for transmission to a debuncher 52 through a quadrapole 54. The debuncher functions to reduce the momentum spread of the beam to approximate the design momentum spread of a beam for injection into the accelerator 12 through a quadrapole 56, vertical and horizontal beam directing dipoles 58 and 60, a reverse septum magnet and injection septum 62 and final injection kicker 64. The reverse septum magnet functions to bend the injection beam 25 degrees upward while the injection septum bends the beam 20 degrees downward, the kicker bending the beam another 5 degrees downward to the injection port of the accelerator 12.

The accelerator 12 is a synchroton containing ring dipoles, zero-gradient dipoles with edge focusing (A magnets) 66–73, vertical trim dipoles 74–77, horizontal trim dipoles 78–81, trim qudrupoles 82–85 and extraction Lambertson magnets 86. The A magnets are the main bending and focusing magnets of the synchroton and have the performance specifications listed in Table V. The A magnets are built curved through a 45 degree arc. The horizontal trim dipoles 78–81 are designed to displace the beam horizontally about plus or minus 4 cm at 250 MeV. The vertical trim dipoles are similar in concept, but with an integrated strenght of 0.018 T-m and a vertical displacement of plus or minus 2 cm at 250 MeV. All trim dipoles are located in the four long straight sections of the synchrotron and are individually controllable through programmable power supplies and shunts. The four trim quadrupoles 82–85 are located in the four short straight sections of the synchrotron with apertures sufficiently large to enclose beam monitors. The trim quadrupoles are also used to excite half-integer resonance during extraction of the beam from the synchrotron. The extraction Lambertson magnet 86 is a small aperture dc vertical dipole for bending the beam to be extracted downward out of the synchrotron.

The parameters for the acceleration system are set forth in Table VI and Appendix I. To accelerate the proton beam to 250 MeV in 0.5 seconds requires an energy gain of 90 eV per turn. An rf system including an rf cavity 87 is used to accelerate the beam into extraction and to reduce the momentum spread of the extracted beam.

The parameters for beam extraction are set forth in Table VII and Appendix I. The beam is slow extracted from the synchrotron by horizontal half-integer resonant extraction. The tune is brought to the resonance value of 0.5 by the extraction quadrupoles 82–85. The beam is accelerated by the rf system to a electrostatic wire septum, stepped horizontally across it by the resonant amplitude growth and deflected horizontally past an iron septum in the Lambertson magnet 86. The beam is bent down 10.5 degrees by the Lambertson magnet and if not bent back to the horizontal continues straight down to a beam dump embedded in the floor housing the system. A second verticle dipole 88 similar to the Lambertson but without the septum (Dogleg Lambertson) is used to deflect the beam back to the horizontal plane for transport down the beam line to the beam transport system 16 including the switching magnets 38–44.

As previously described, the beam transport system 16 includes the switchyard 36 and the gantries 28, 30 and 32. The switchyard includes the switching magnets 38–44 and the other magnets illustrated in FIG. 1. In passing from the accelerator 12, the beam is directed through four quadrupoles to the switching magnet 38, the general function of which has been previously described. All of the switching magnets are substantially the same in structure, function and control. Accordingly, only the switching magnet 38 will be described in detail. Refering to FIG. 7, the switching magnet is a type A' bending magnet. That is, it is similar to the previously described type A magnets with the addition of switch control features. The type A' magnet is an electromagnet configured to bend a beam of protons of a specified momentum (energy) through an angle of 45 degrees when current in a coil of the magnet is controlled to a precise current required for that momentum. When the magnet is not so energized, the protons proceed in a straight line through a hole provided in the yoke of the magnet to the next energized A' magnet. As illustrated, control of the magnet is achieved by either (i) energizing a contactor 89 which turns on a direct current power supply 90 and concurrently sending a digitized current setting to the power supply to require the supply to regulate at a prescribed current, or (ii) opening the contactor to turn off the supply. The controls are initated by a control computer 94 which initiates digital commands to a VME buss crate 95 (see FIG. 6). This unit then controls and monitors the operation of the power supply as indicated by the leads 91, 92 and 93.

With respect to the treatment stations 18, 20 and 22, the swithyard 36 includes the same basic components functioning in substantially the same manner. Therefore, only the structure and operation of the switchyard components relative to the treatment station 18 will be described in detail. As illustrated most clearly in FIGS. 3 and 5, the switching magnet 38 combines with the optics carried by the gantry 28 to include two A' dipoles 38 and 39, a chain of six rotator quadrupoles 96, three B dipoles 97, 98 and 99 and quadrupole doublets 100 and 101. The structure and operation of the gantry 28 is the same for the gantries 30 and 32 and may conform to the gantry described in a publication of the Harvard Cyclotron Laboratory entitled "Preliminary Design Study for a Corkscrew Gantry" authored by A. M. Koehler and an application for United States patent entitled "Beam Redirecting" filed by Harvard University, Boston, Mass.

With the switching magnet 38 and the switchyard 36 configured as described above for the treatment station 18, the proton beam upon entering the magnet 38 is bent 45 degrees to enter the magnet 39 where it is bent another 45 degrees to exit along an axis of rotation 102 for the gantry 28. After passing through the rotator quadrupoles 96 along the axis 102, the beam is directed by the magnet 97, 90 degrees away from the axis to and through the quadrupole doublet 100 to the magnet 98. In the magnet 98 the beam is bent 90 degrees to pass through the quadrupole doublet 101 to the magnet 99. In the magnet 99, the beam is bent another 90 degrees to return on a path perpendicular to and intersecting the axis 102 at a target isocenter 103 within a patient supported in a fixed orientation on the table 34 in the treatment station 18. With rotation of the gantry 28 about the axis 102 pursuant to the aforementioned Harvard University publication and patent application, the beam is delivered to the target isocenter 103 from several different angles to provide a desired treatment for the patient. By selective control of the switching magnets and switchyard components associated with the treatment stations 20 and 22, similar treatment may be provided to patients in such stations.

Figure 6:
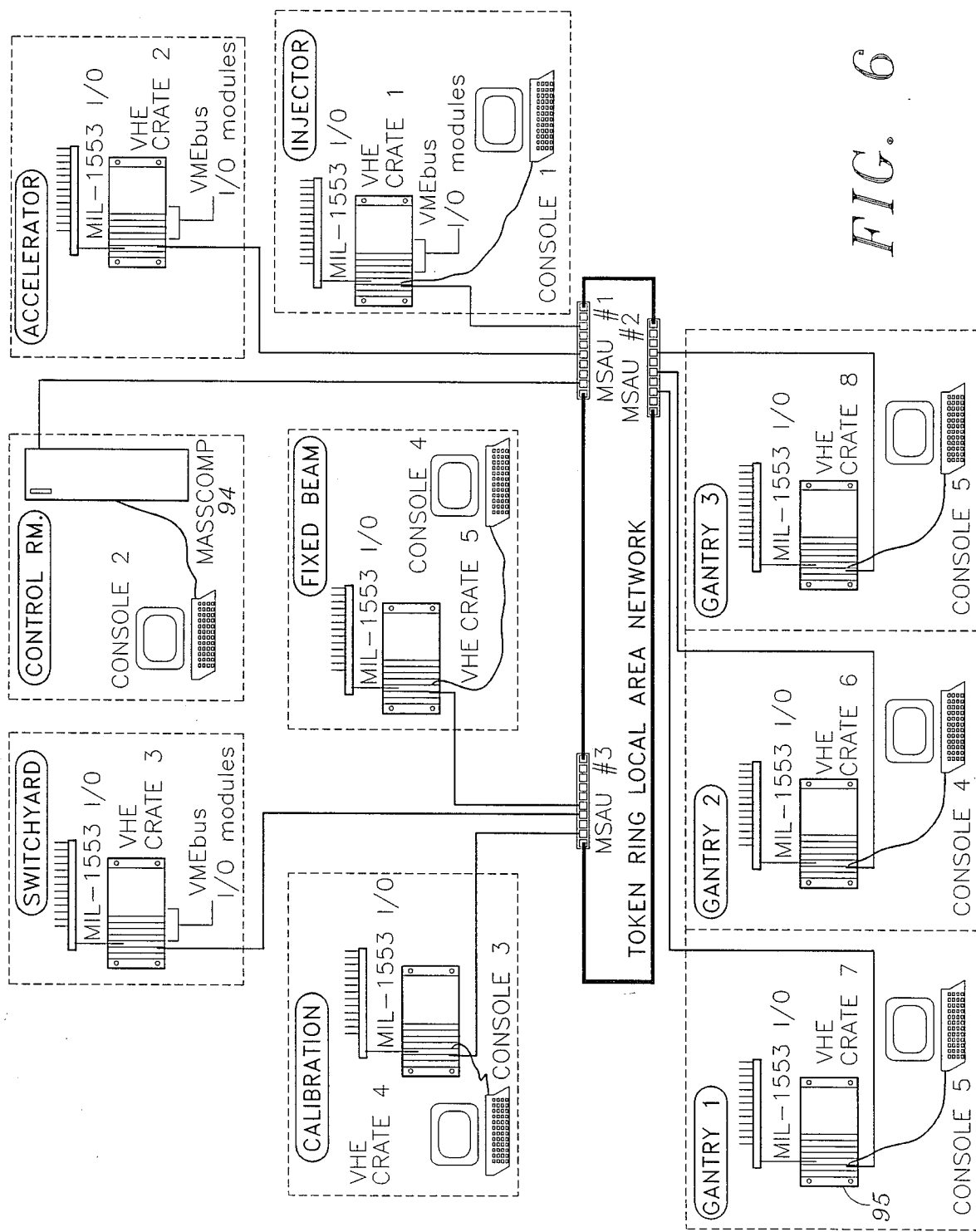
FIG. 6 is a diagram of the control system for the proton beam system of FIG. 1.
Figure 7:
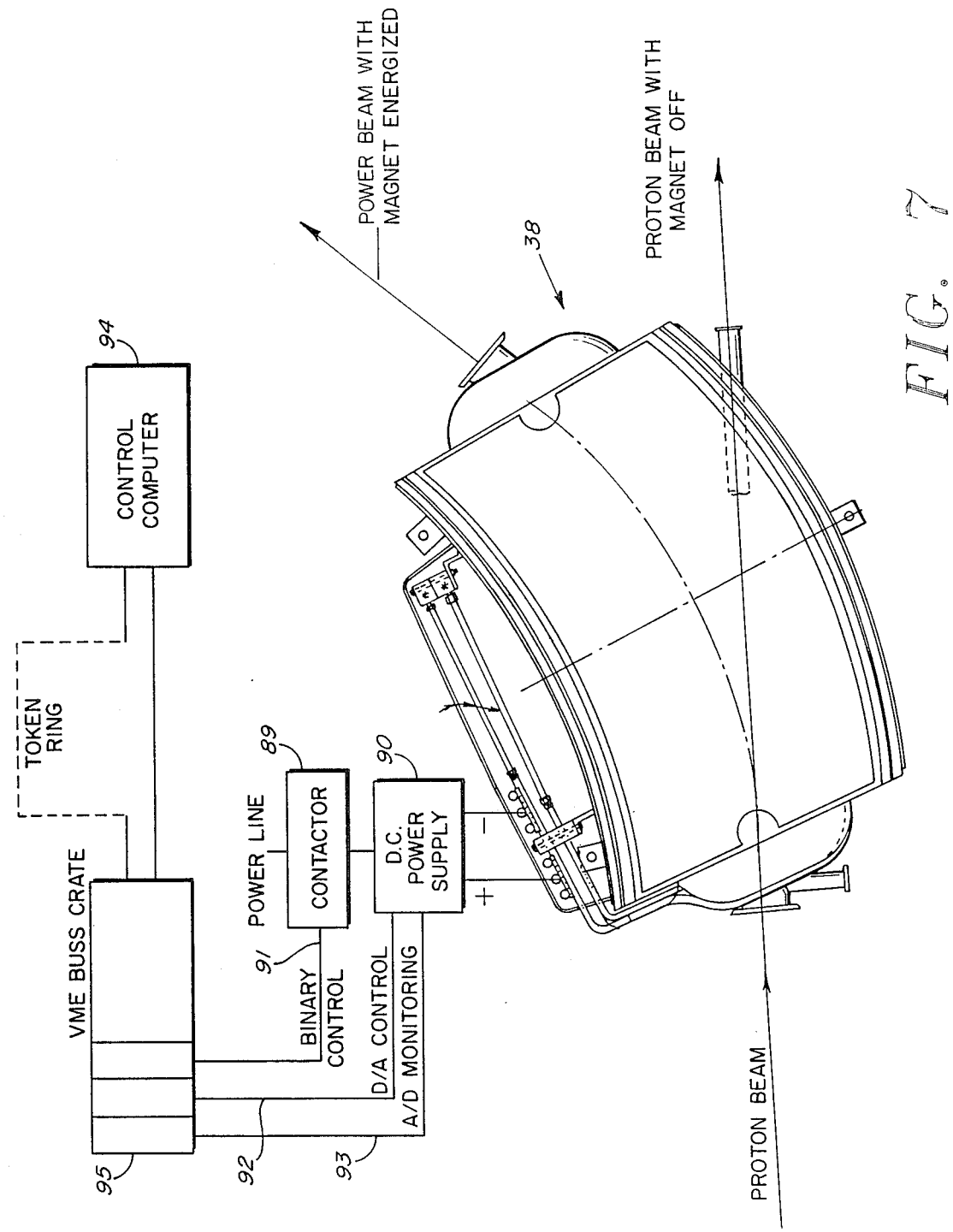
FIG. 7 is a plan view of a switching magnet and a portion of the control system of FIG. 6 for selectively controlling operation of the switching magnet.

As previously stated, the entire system as described herein is under regulation and operator control through the control system illustrated in FIG. 6. The control system is patterned after the system used for the Fermilab 200 MeV linac. It consists of multiple distributed microprocessor-based systems networked together and to a central MASSCOMP computer 94 using the IEEE-802.5 Local Area Network (LAN) Standard. LAN is the Token Ring protocol supported by IBM. Three 68000-based local stations are used in the control system. The MASSCOMP performs the centralized coordination of beam requests from the treatment stations in the therapy system as well as programmed beam-energy control. The MASSCOMP includes disks and printers for storing operating conditions and copies of the data bases used in the local stations. The control system also provides timing pulses to the entire therapy system.

The local stations use VMEbus (IEEE-1014) hardware and Motorola 68000 processors. Each local station contains a CPU card, a network adapter and a non-volatile RAM card to store the local data base of descriptors and parameters associated with the equipment controlled by that station. The remaining cards are analog and binary input and output interface cards that read and set parameters in the accelerator equipment. The major hardware components controlled by the local stations are the ion source 10, the injector 14, and accelerator 12 and the switiching magnets.

The Token Ring is a recent network standard that is well supported by IBM and others. A twisted-pair cable forms the physical ring. Wiring concentrators provide access to the ring by the local station consoles.

APPENDIX I
ACCELERATOR PARAMETERS

LATTICE

| | |
|---|---|
| Injection energy $T_i$ | 1.7 Mev |
| Extraction energy $T_e$ | 70–250 MeV |
| Circumference $2\pi R$ | 20.053 m |
| Equivalent radius R | 3.1915 m |
| No. of sectors | 4 |
| Long straight section (L) length $l_L$ | 2.0 m |
| Short straight section (S) length $l_s$ | 0.5 m |
| Magnet (B) length $l_B$ | 1.2566 m |
| Sector structure | L/2 BSB L/2 |
| Magnet bend angle $\theta_B$ | $\pi/4$ |
| Magnet bend radius $\rho$ | 1.6 m |
| Magnet edge angle $\theta_e$ | 0.328 rad (18.8°) |
| Magnet gradient | 0 |
| Injection field $B_i$ | 0.118 T |
| Extraction field $B_e$ | 0.77–1.52 T |
| Horizontal tune $\nu_x$ | 0.600 |
| Vertical tune $\nu_y$ | 1.322 |
| Horizontal Amplitude function $\beta_x$ | |
| Mid-L | 4.86 m |
| Mid-S | 5.25 m |
| Maximum (Mid-B) | 5.98 m |
| Vertical amplitude function $\beta_y$ | |
| Mid-L | 1.88 m |
| Mid-S | 3.16 m |
| Maximum (End-S) | 3.18 m |
| Dispersion function D | |
| Mid-L | 8.98 m |
| Mid-S | 8.98 m |
| Maximum (Mid-B) | 9.59 m |
| Transition $\gamma_t$ | 0.5832 |
| Magnet pole gap | 5.0 cm |
| Magnet pole tip width | 20.0 cm |
| Good field aperature | 5.0 cm (V) by 10.0 cm (H) |
| Space Charge | |
| Maximum beam size | ±2.25 cm (V) by ±4.5 cm (H) |
| Average beam size | ±1.98 cm (V) by ±4.24 cm (H) |
| Bunching factor B | 2 |
| Tune shift allowed $\delta\nu$ | 0.15 |

APPENDIX I
ACCELERATOR PARAMETERS

LATTICE

| | |
|---|---|
| Space-charge intensity limits (uniform beam) | $3 \times 10^{11}$ protons |
| Average beam current at 2-sec cycle time, which gives 24 nA | 24 nA |
| Longitudinal (Microwave) Instability | |
| At injection $\eta = \|1/\gamma^2 - 1/\gamma_t^2\|$ | 1.93 |
| At bunching factor 2 and $3 \times 10^{11}$ protons | |
| $I_{peak}$ | 86.4 mA |
| $(\Delta p/p)_{peak}$ | $\pm 1/6\%$ |
| $(\Delta p/p)_{FWHM}$ | $3.3 \times 10^{-3}$ |
| Allowed $Z_l/n$ | 850 Ω |
| Transverse (fast head-tail) Instability | |
| With 90 MHz damper (damp up to n = 100) | |
| Allowed $Z_{t\,max}$ | 2.0 MΩ/m |
| Elliptical beam pipe inner dimensions | 4.5 cm × 9.0 cm |
| Equivalent allowed $Z_l/n$ | 20 Ω |
| Injector | |
| Type | RFQ linac |
| Injection energy | 40 keV |
| Final energy | 1.7 MeV |
| RF frequency | 425 MHz |
| RF power | 315 kW |
| Length | 220.5 cm |
| Output beam current | 50 mA |
| Energy spread ΔT/T | |
| before debuncher | ±1% |
| after debuncher | ±1/3% |
| Momentum spread Δp/p | |
| after debuncher | ±1/6% |
| with bunching factor | ±1/3% |
| Emittance $\epsilon_x$, $\epsilon_y$ | $\lesssim 25\,\pi$ mm-mrad |
| Injection | |
| Scheme - vertical upward, kicked onto orbit by a single turn electric kicker. | |
| No. of turns injected | 1 |
| Revolution time at injection | 1.11 μsec |
| No. of protons injected at 43.3 mA | $3 \times 10^{11}$ |
| Kicker field | 36.5 kV/5 cm = 7.3 kV/cm |
| Kicker length | 40 cm |
| Kicker location | 20 cm to 60 cm downstream of mid-point of long straight L1 |
| Point of injection | long straight L1 |
| Kick angle | 5° |
| Kicker fall time | <25 nsec |
| Circulating Injected Beam | |
| Momentum width at B = 2 | ±30 mm |
| Betatron width | ±15 mm |
| Horizontal emittance (acceptance less momentum width) | 38π mm-mrad |
| Betatron height | ±22 mm |
| Vertical emittance (acceptance) | 155π mm-mrad |
| Coupling during acceleration will equalize the two planes to | 96π mm-mrad |
| Acceleration | |
| Cavity type | untuned, ferrite loaded |
| Cavity dimensions | 50 cm (dia) × 60 cm (long) |
| Harmonic number | 1 |
| Frequency range | 0.8987–9.1734 MHz |
| Acceleration time | 0.5 sec |
| Energy gain per turn | 90.0 eV |
| Peak voltage | 330 V |
| Synchronous phase | 16° |
| Cavity location | upstream L4 |
| Extraction | |
| Scheme: Horizontal ½-integer ($\nu_x = 0.5$) resonant extraction with electrostatic wire septum and Lambertson septum. | |
| Extracts downward in L2 | |
| Horizontal beam max. half-width ($\beta_{x\,max} = 6.0$ m, $D_{max} = 9.6$ m) | |

| | 70 Mev | 250 MeV |
|---|---|---|
| $\epsilon_x$ (π mm-mrad) | 5.8 | 2.9 |
| $a_\beta$ (mm) | 5.9 | 4.2 |
| Δp/p | $6 \times 10^{-4}$ | $3 \times 10^{-4}$ |
| $a_p$ (mm) | 5.7 | 2.9 |
| $a_\beta + a_p$ (mm) | 11.6 | 7.1 |

| | |
|---|---|
| Betatron tunes at extraction | |
| Horiz./vert. $\nu_x/\nu_y$ | 0.5/1.36 |

APPENDIX I
ACCELERATOR PARAMETERS

LATTICE

Excitation quadrupole

| | |
|---|---|
| Field gradient (max) | 4 T/m |
| Length | 10 cm |
| Aperature | full |
| Number and location | 4 in short straight sections |

Electrostatic Wire septum

| | |
|---|---|
| Location | L3 |
| Horizontal aperture | 1.3 cm |
| Length | 10 cm |
| Field | 45 kV/cm |
| Deflection angle | 1.0 mrad (inward) |
| Position of septum | −3 cm from orbit |
| Width of gap at Lambertson | ~4 mm |

Lambertson septum

| | |
|---|---|
| Field | 8 kG |
| Length | 50 cm |
| Aperture | 1.5 cm (H) × 5 cm (V) |
| Deflection Angle | 0.165 rad (9.45°)(downward) |
| Location | upstream L2 |

Steering dipoles (all long straight sections)

*Horizontal*

| | |
|---|---|
| Number | 4 |
| Max. field times length | ±0.025 Tm |
| Max. orbit deflection at 250 MeV | ±4.5 cm |

*Vertical*

| | |
|---|---|
| Number | 4 |
| Max. field | ±0.02 Tm |
| Max. orbit deflection at 250 MeV | ±2.25 cm |

Beam position monitors

| | |
|---|---|
| Number | 8 |
| Location | in all long & short straight sections |

APPENDIX II
INJECTION-SYSTEM PARAMETERS

Source

| | |
|---|---|
| Type | Duoplasmatron |
| Energy | 40 keV |
| Peak Current | 55 mA |
| Pulse Length | 30 μsec |
| Emittance | 100π mm mrad |

Low-Energy Transport

| | |
|---|---|
| Focusing | Solenoidal |
| Peak Fields | 0.7 T on axis |
| Beam Chopper Pulse Length | 1.1 μsec |

RFQ

| | |
|---|---|
| Input Energy | 40 keV |
| Output Energy | 1.7 MeV |
| Input Emittance | 100π mm-mrad |
| Output Emittance | ≤25 π mm-mrad |
| Initial Energy Spread | 0 |
| Final Energy Spread | ±18 keV (±26° phase spread) |
| RF Pulse Length | ~100 μsec |
| Aperature | 4.64 mm |
| Radial Matcher Length | 1.9 cm |
| Shaper Length | 44.2 cm |
| Buncher Length | 12.7 cm |
| Accelerator Length | 161.7 cm |
| Total Length | 220.5 cm |
| Peak Power | 315 kW |
| Average Power | 158 W |
| Frequency | 425 MHz |
| Surface Field | 38 MV/m |
| Vane-Vane Voltage | 59 kV |
| Van-tip radius | 0.232 cm |
| Nominal Input Current | 50 mA |
| Transmission | 93% |
| Transverse Acceptance | 160π mm-mrad (at zero current) |
| rms Emittance Increase | 20% (based on an input 95% contour emittance of 54π mm mrad) |
| Output Energy Spread | ±18 keV |
| Output Phase Spread | ±26 degrees |
| Input Beam Parameters | $\beta_x = 4.0$ cm, $\alpha_x = 2.0$ |
| | $\beta_y = 4.0$ cm, $\alpha_y = 2.0$ |
| Output Beam Parameters | $\beta_x = 9.0$ cm, $\alpha_x = -1.7$ |
| | $\beta_y = 12.0$ cm, $\alpha_y = 2.2$ |
| Focusing Parameter B | 5.829 |
| $\phi_s$ at end of buncher | −50° |
| $\phi_s$ at end of accelerator | −40° |

High-Energy Transport

| | |
|---|---|
| Focusing | Quadrupoles |
| Peak Gradients | 3 T/m |
| Drawing No. | BT-100 |

Debuncher

| | |
|---|---|
| Drift Length | 220 cm |
| Cavity Length | 25 cm |
| Aperature | 2.4 cm |
| Initial Momentum Spread | ±0.5 × 10⁻² |
| Final Momentum Spread | ±1.7 × 10⁻³ |
| Peak Power | ~500 W |

Ring Inflection System

| | |
|---|---|
| Type | Vertical dogleg |
| Bending | Magnetic |
| Field | 0.26 T |
| Bend Angle | 25° up, 20° down |
| Aperture | 3 cm × 3 cm |

Kicker

| | |
|---|---|
| Type | Electrostatic |
| Bend | 5° down |
| Pulse Length | 1.1 μsec |
| Voltage | 36.5 kV |
| Field | 7.3 kV/cm |
| Fall Time | 50 nsec |

Reverse Septum Magnet

| | | |
|---|---|---|
| (Injection Energy) | (3 MeV) | (1.7 MeV) |
| Maximum Field | 3.443 kG | 2.590 kG |

APPENDIX II
INJECTION-SYSTEM PARAMETERS

| | | |
|---|---|---|
| Magnet Length | 31.75 cm | |
| Bending Radius | 72.7 cm | |
| Bending Angle | 25° | |
| Aperture Width | 3 cm | |
| Aperture Height | 3 cm | |
| Septum Thickness | 0.47 cm | |
| Coil Inductance | 0.4 μH | |
| Coil Resistance (20° C.) | 250 μΩ | |
| Peak Pulse Current | 8220 A | 6634 A |
| Drive Frequency | 1200 Hz | |
| Pulse Interval | 2 sec | |
| Pulse Duration | 416 μsec | |
| Duty Factor | 0.02% | |
| Coil Av. Power | 1.8 W | 1.0 W |
| Pressure on Conductor | 94278 Nt/m² (13.7 psi) | |
| Copper Deflection between Gap | 0.0137 mm (0.00054 in.) | |
| Injection Septum Magnet | | |
| (Injection Energy) | (3 MeV) | (1.7 MeV) |
| Maximum Field | 3.443 kG | 2.590 kG |
| Magnet Length | 25.4 cm | |
| Bending Radius | 72.7 cm | |
| Bending Angle | 20° | |
| Aperture Width | 3 cm | |
| Aperture Height | 3 cm | |
| Septum Thickness (with shield) | 0.6 cm | |
| Coil Inductance | 0.319 μH | |
| Coil Resistance (20° C.) | 200 μΩ | |
| Peak Pulse Current | 8220 A | 6634 A |
| Current Drive Frequency | 1200 Hz | |
| Pulse Interval | 2 sec | |
| Pulse Duration | 416 μsec | |
| Duty Factor | 0.02% | |
| Coil Average Power | 1.4 W | 0.8 W |
| Pressure on Conductor | 94278 Nt/m² (13.7 lb/in²) | |
| Copper Deflection between Gap | 0.0137 mm (0.00054 in.) | |

TABLE I
Accelerator Performance Specifications

| | |
|---|---|
| Particle | Protons |
| Energy | 70–250 MeV (continuously variable) |
| Cycle Time | 2 sec (nominal) |
| Acceleration Time | 0.5 sec |
| Flattop Time | 1 sec |
| Return Time | 0.5 sec |
| Intensity | >1.6 × 10¹¹ per cycle |
| Beam Uniformity | <±2.5% throughout extraction |
| Extraction Efficiency | >95% |

TABLE II
Orbit Parameters

LATTICE

| | |
|---|---|
| Injection energy $T_i$ | 1.7 Mev |
| Extraction energy $T_e$ | 70–250 MeV |
| Circumference $2\pi R$ | 20.053 m |
| Equivalent radius R | 3.1915 m |
| No. of sectors | 4 |
| Long straight section (L) length $l_L$ | 2.0 m |
| Short straight section (S) length $l_s$ | 0.5 m |
| Magnet (B) length $l_B$ | 1.2566 m |
| Sector structure | L/2 BSB L/2 |
| Magnet bend angle $\theta_B$ | $\pi/4$ |
| Magnet bend radius $\rho$ | 1.6 m |
| Magnet edge angle $\theta_e$ | 0.328 rad (18.8°) |
| Magnet gradient | 0 |
| Injection field $B_i$ | 0.118 T |
| Extraction field $B_e$ | 0.77–1.52 T |
| Horizontal tune $\nu_x$ | 0.600 |
| Vertical tune $\nu_y$ | 1.322 |
| Horizontal Amplitude function $\beta_x$ | |
| Mid-L | 4.86 m |
| Mid-S | 5.25 m |
| Maximum (Mid-B) | 5.98 m |
| Vertical amplitude function $\beta_y$ | |
| Mid-L | 1.88 m |
| Mid-S | 3.16 m |
| Maximum (End-S) | 3.18 m |
| Dispersion function D | |
| Mid-L | 8.98 m |
| Mid-S | 8.98 m |
| Maximum (Mid-B) | 9.59 m |
| Transition $\gamma_t$ | 0.5832 |
| Magnet pole gap | 5.0 cm |
| Magnet pole tip width | 20.0 cm |
| Good field aperature | 5.0 cm (V) by 10.0 cm (H) |
| Circulating Injected Beam | |
| Momentum width at bunching factor 2 | ±30 mm |
| Betatron width | ±15 mm |
| Horizontal emittance (acceptance less momentum width) | 38π mm-mrad |
| Betatron height | ±22 mm |
| Vertical emittance (acceptance) | 155π mm-mrad |
| Coupling during acceleration will equalize the two planes to | 96π mm-mrad |

TABLE III
Intensity Parameters

| | |
|---|---|
| Space Charge | |
| Maximum beam size | ±2.25 cm (V) by ± 4.5 cm (H) |
| Average beam size | ±1.98 cm (V) by ± 4.24 cm (H) |
| Bunching factor B | 2 |
| Tune shift allowed $\delta\nu$ | 0.15 |
| Space-charge intensity limit (uniform beam) | 3 × 10¹¹ proton |
| Average Current at 2-sec cycle time | 24 nA |
| Longitudinal (Microwave) Instability | |
| At injection $\eta = \|1/\gamma^2 - 1/\gamma_t^2\|$ | 1.93 |
| At bunching factor 2 and 3 × 10¹¹ protons | |
| $I_{peak}$ | 86.4 mA |
| $(\Delta p/p)_{peak}$ | ⅜% |
| $(\Delta p/p)_{FWHM}$ | ⅓% |
| Allowed $Z_l/n$ | 850 Ω |
| Transverse (fast head-tail) Instability | |
| With 90-MHz damper (damp up to n = 100) | |
| Allowed $Z_t$ | 2.0 MΩ/m |
| Elliptical beam pipe inner dimensions | 4.5 cm × 9.0 cm |
| Equivalent allowed $Z_l/n$ | 20Ω |

TABLE IV
Injection Parameters

| | |
|---|---|
| Source | 40 keV Duoplasmatron |
| Injector Type | RFQ Linac |
| Energy | 1.7 MeV |
| Beam Pulse Length (after chopper) | 1.1 μsec |

TABLE IV-continued

| Injection Parameters | |
|---|---|
| Peak Output Current | 50 mA |
| Momentum Spread $\Delta p/p$ | 1% (RFQ Output) |
| | ½% (after Debuncher) |

TABLE V

| Synchrotron Ring Dipole Performance Specifications | |
|---|---|
| Injection Field | 0.118 T |
| Peak Field | 1.52 T |
| Duty Factor | 50% |
| Ramp Slope | 2.8 T/sec |
| Allowable Current Error | 0.1% |

TABLE VI

| Acceleration System Parameters | |
|---|---|
| Acceleration | |
| Cavity type | untuned, ferrite loaded |
| Cavity dimensions | 50 cm (dia) × 60 cm (long) |
| Harmonic number | 1 |
| Frequency range | 0.8987–9.1734 MHz |
| Acceleration time | 0.5 sec |
| Energy gain per turn | 90.0 eV |
| Peak voltage | 330 V |
| Synchronous phase | 16° |
| Cavity location | upstream L4 |

TABLE VII

Extraction Parameters

Scheme: Horizontal ½-integer ($\nu_x = 0.5$) resonant extraction with electrostatic wire septum and Lambertson septum.
Extracts downward in L2
Horizontal beam max. half-width
($\beta_{x\ max} = 6.0$ m, $D_{max} = 9.6$ m)

| | 70 Mev | 250 MeV |
|---|---|---|
| $\epsilon_x$ ($\pi$ mm-mrad) | 5.8 | 2.9 |
| $a_\beta$ (mm) | 5.9 | 4.2 |
| $\Delta p/p$ | $6 \times 10^{-4}$ | $3 \times 10^{-4}$ |
| $a_p$ (mm) | 5.7 | 2.9 |
| $a_\beta + a_p$ (mm) | 11.6 | 7.1 |

| Betatron tunes at extraction | |
|---|---|
| Horiz./vert. $\nu_x/\nu_y$ | 0.5/1.36 |
| Excitation quadrupole | |
| Field gradient (max) | 4 T/m |
| Length | 10 cm |
| Aperture | full |
| Number and location | 4 in short straight sections |
| Electrostatic Wire septum | |
| Location | L3 |
| Horizontal aperture | 1.3 cm |
| Length | 10 cm |
| Field | 45 kV/cm |
| Deflection angle | 1.0 mrad (inward) |
| Position of septum | −3 cm from orbit |
| Width of gap at Lambertson | ~4 mm |
| Lambertson septum | |
| Field | 8 kG |
| Length | 50 cm |
| Aperture | 1.5 cm(H) × 5 cm(V) |
| Deflection Angle (downward) | 0.165 rad (9.45°) |
| Location | upstream L2 |

We claim:

1. A proton beam therapy system comprising:
a plurality of separate patient treatment stations each having a patient support for orienting a patient in a fixed position;
a source of protons;
an accelerator for accelerating protons as a beam;
an injector for transporting protons from the source to the accelerator;
a proton beam transport system for directing proton beams from the accelerator to the treatment stations to treat patients supported in fixed orientations by the patient supports, the proton beam transport system comprising
a gantry at each treatment station each rotatable about a different axis of rotation and carrying optics for receiving a proton beam on its axis of rotation, transporting the proton beam away from the axis of rotation and returning the proton beam on a path perpendicular to and intersecting the axis at a target isocenter within the patient whereby with rotation of the gantry the proton beam is delivered to the target isocenter from several different angles and
a switchyard including a first multistate switching magnet for receiving the proton beam from the accelerator and in a first state bending and delivering the proton beam to the optics carried by a first gantry at a first one of the treatment stations along the axis of rotation of the first gantry and in a second state passing the proton beam to a second one of the treatment stations; and
a control system for the proton beam therapy system including an operator controllable means for (1) selectively switching the first switching magnet between its first and second states and (2) controlling the rotational position of the first gantry to direct the proton beam exiting the first switching magnet in its first state to the target isocenter for the first treatment station along one or more controlled angles.

2. The proton beam therapy system of claim 1 further comprising:
a second switching magnet in the switchyard for receiving the proton beam from the first switching magnet when in its second state, the second switching magnet being characterized by a first state for bending and delivering the proton beam to the optics carried by a second gantry at a second one of the treatment stations along the axis of rotation of the second gantry, and a second state for passing the proton beam to a third one of the treatment stations,
and wherein the operator controllable means of the control system (1) switches the first and second switching magnets between their first and second states and (2) controls the rotational positions of the gantry at each of the first and second treatment stations to direct the proton beam exiting the one of the first and second switching magnets in its first state to the target isocenter for the associated treatment station at one or more angles.

* * * * *